US006979424B2

(12) United States Patent
Northrup et al.

(10) Patent No.: US 6,979,424 B2
(45) Date of Patent: Dec. 27, 2005

(54) INTEGRATED SAMPLE ANALYSIS DEVICE

(75) Inventors: M. Allen Northrup, Berkeley, CA (US); Kurt E. Petersen, San Jose, CA (US); William A. McMillan, Cupertino, CA (US); Gregory T. A. Kovacs, Stanford, CA (US)

(73) Assignee: Cepheid, Sunnyvale, CA (US)

( * ) Notice: Subject to any disclaimer, the term of this patent is extended or adjusted under 35 U.S.C. 154(b) by 314 days.

(21) Appl. No.: 09/929,270

(22) Filed: Aug. 13, 2001

(65) Prior Publication Data

US 2002/0025576 A1 Feb. 28, 2002

Related U.S. Application Data

(63) Continuation of application No. 09/271,411, filed on Mar. 17, 1999, which is a continuation-in-part of application No. 09/040,498, filed on Mar. 17, 1998, now abandoned.

(51) Int. Cl.[7] .................. G01N 1/00; G01N 15/00; B01J 8/00; C12Q 1/68
(52) U.S. Cl. .................. 422/50; 422/68.1; 422/129; 435/4; 435/6; 435/7.1
(58) Field of Search .................. 422/50, 68.1, 129; 435/6, 7.1, 4

(56) References Cited

U.S. PATENT DOCUMENTS

| | | | |
|---|---|---|---|
| 5,480,614 A | 1/1996 | Kamahori | 422/70 |
| 5,587,128 A | 12/1996 | Wilding et al. | 422/50 |
| 5,589,136 A | 12/1996 | Northrup et al. | 422/102 |
| 5,646,039 A | 7/1997 | Northrup et al. | 435/287.2 |
| 5,744,366 A | 4/1998 | Kricka et al. | 436/63 |
| 5,824,204 A | 10/1998 | Jerman | 204/601 |
| 5,849,208 A | 12/1998 | Hayes et al. | 216/94 |
| 5,856,174 A | 1/1999 | Lipshutz et al. | 435/286.5 |
| 6,074,827 A * | 6/2000 | Nelson et al. | 435/6 |

OTHER PUBLICATIONS

Waters et al., "Microchip Device for Cell Lysis, Multiplex PCR Amplification, and Electrophoretic Sizing", *Anal. Chem.* 1998, 70, 158-162.
Woolley et al., "Functional Integration of PCR Amplification and Capillary Electrophoresis in a Microfabricated DNA Analysis Device", *Anal. Chem.* 1996, 68, 4081-4086.
Webster et al., "Large-Volume Integrated Capillary Electrophoresis Stage Fabricated Using Micromachining of Plastics on Silicon Substrates", *International Conference on Solid-State Sensors and Actuators* (Transducers '97) (Chicago) pp. 503-506, 1997.

* cited by examiner

*Primary Examiner*—Ardin H. Marschel
(74) *Attorney, Agent, or Firm*—Townsend and Townsend and Crew LLP

(57) ABSTRACT

An analysis device comprises a body having a reaction chamber for chemically reacting a sample, a separation region for separating components of the sample, and a transition region connecting the reaction chamber to the separation region. The transition region includes at least one valve for controlling the flow of fluid between the reaction chamber and the separation region. Further, the transition region thermally isolates the reaction chamber from the separation region. In a preferred embodiment, the reaction chamber is an amplification chamber for amplifying nucleic acid in the sample, and the separation region comprises an electrophoresis channel containing a suitable matrix material, such as electrophoresis gel or buffer, for separating nucleic acid fragments. Electrodes are embedded in the body for separation of sample components. The body may also be surrounded by external, functional components such as an optical detector for detecting separated components of the sample.

6 Claims, 7 Drawing Sheets

INTEGRATED SAMPLE ANALYSIS DEVICE

RELATED APPLICATION INFORMATION

This application is a continuation of U.S. application Ser. No. 09/271,411 filed Mar. 17, 1999 which application is a continuation-in-part of U.S. application Ser. No. 09/040,498 filed Mar. 17, 1998, now abandoned. All of these applications are incorporated by reference herein for all purposes.

FIELD OF THE INVENTION

The present invention relates generally to the field of chemical processing, and in particular to an integrated device for analyzing a sample.

BACKGROUND OF THE INVENTION

There are many applications in the field of chemical processing in which it is desirable to separate chemical components prior to or after reacting chemicals. Examples of reactions requiring separation of components include organic, inorganic, biochemical, and molecular reactions. Examples of chemical reactions include thermal cycling amplification, such as polymerase chain reaction (PCR), ligase chain reaction (LCR), isothermal nucleic acid amplification, self-sustained sequence replication, enzyme kinetic studies, homogeneous ligand binding assays, affinity binding assays, and more complex biochemical mechanistic studies. Conventional separation techniques include electrophoresis, such as capillary electrophoresis, synchronized cyclic electrophoresis, and free flow electrophoresis. Conventional separation techniques also include isoelectric focusing (IEF), hybridization, liquid and gas chromatography, molecular sieving and filtering.

Components to be separated in various samples include nucleic acids, amino acids, peptides, proteins, cells, viruses, bacteria, organic compounds, carbohydrates, etc. For example, in amplification applications, multiple oligonucleotide primers and probes designed for many organisms can be used to multiply DNA from numerous organisms in a sample. After amplification, separation techniques such as electrophoresis or IEF can be employed to separate the amplification products by certain properties, such as molecular weight, for subsequent detection by fluorescence methods.

Of increasing interest in the field of chemical separation is the use of devices that include an integrated reaction chamber and separation region. Such integrated devices provide a number of advantages over conventional devices in which one transfers a fluid sample between a reaction apparatus and a separation device. For example, where the chemical reaction and separation steps are performed in a single integrated device, one may avoid contamination and crossover of sample or reaction products. In addition, an integrated device may allow for substantially faster sample processing and analysis.

Recent efforts to integrate processing and analytical functionalities in a single device, especially in the field of MEMS, microfabrication, and microfluidics, have resulted in the development of devices that include multiple substrates bonded together. The substrates are usually bonded with adhesives, or by heat sealing, fusion bonding, or anodic bonding. These multi-substrate devices typically include a reaction chamber that is connected to a separate separation component, such as a capillary tube containing a suitable electrophoresis gel, by an adhesive such as epoxy. Alternatively, these multi-substrate devices have reaction chambers and separation channels etched into a plate and a cover bonded over the top of the plate. For example, U.S. Pat. No. 5,849,208 issued to Hayes et al. discloses such a multi-substrate device.

Unfortunately, prior integrated devices provide for only limited control of fluid between reaction and separation regions. For example, high internal pressure can develop in a reaction chamber due to the thermal expansion of liquid or gas present in this region, the generation of gas bubbles, or the chemical reactions performed inside of the chamber. This pressure, combined with any elevated temperatures within the chamber, can have detrimental effects on fluidic components and performance upstream and downstream from the reaction chamber. A particular problem is the flow or diffusion of chemicals from the reaction chamber into unwanted regions caused by the elevated pressure or temperature. This situation is especially problematic when sensitive detection methods and apparatus are located downstream from the reaction chamber.

A further problem with prior integrated devices is that when the reaction chamber is heated to perform a chemical reaction, the separation region is also heated due to thermal conduction. If the separation region is heated, however, the separation material contained in the region, e.g., electrophoresis gel, degrades and renders the device inoperable. In addition to degrading the separation material, the thermal conduction between the reaction chamber and separation region causes large thermal gradients within the device and prevents adequate heating of a sample in the reaction chamber.

Moreover, where the separation region requires electrodes, as in capillary electrophoresis, micro-electrophoresis, and IEF, there are many issues that have not been addressed by prior art designs. Much of the prior art has focused on issues regarding the design, fabrication, and operation of the capillary channel itself. In contrast, the design of the electrodes which are in contact with the fluid, and which are responsible for the electrokinetic movement of the fluid, has not yet been adequately addressed. The correct design of these electrodes is necessary for the proper, practical, and cost-effective implementation of high-volume, disposable systems that incorporate both reaction chambers and separation regions in a single device. Current state-of-the-art is to incorporate large, open reservoirs (100 $\mu$L or more) near the end of each capillary channel, and then "dip" a separate metal electrode into each open reservoir. This arrangement may be unsuitable for mass production of disposable assemblies. Furthermore, external electrodes, which are placed in contact with the fluid in the disposable assembly, are generally not practical because they may need to be cleaned or otherwise "prepared" prior to each use.

SUMMARY

The present invention provides an integrated reaction and separation device that overcomes the disadvantages of the prior art discussed above.

In a preferred embodiment, the device comprises a body, preferably a molded polymeric part, having a reaction chamber for chemically reacting a sample, a separation region for separating components of the sample, and a transition region connecting the reaction chamber to the separation region. The reaction chamber, transition region, and separation region are formed in and enclosed by the body. Additionally, the transition region includes at least one flow restrictor for controlling the flow of fluid between the reaction chamber and the separation region. Further, the transition region substantially thermally isolates the reaction chamber from the separation region.

The body may be surrounded by external, functional components such as differential pressure sources, electromotive sources, heaters, light sources, and optical detectors. In the preferred embodiment, the reaction chamber is an amplification chamber for amplifying nucleic acid in the sample. Also in the preferred embodiment, the separation region comprises an electrophoresis column or capillary containing a suitable matrix material, such as electrophoresis gel or buffer, for separating nucleic acid fragments in the sample.

A more complete understanding of the present invention may be gained upon consideration of the following description and the accompanying drawings.

BRIEF DESCRIPTION OF THE DRAWINGS

FIG. 3A shows a constrictor in the transition region.

DETAILED DESCRIPTION

The present invention provides an integrated device for the processing of a fluid sample. The device comprises a reaction chamber, a product separation region, and a fluid transition region connecting the reaction chamber to the separation region. In operation, a fluid sample is moved from one region to another and the sample flow is controlled between regions. There may be more than one reaction chamber, transition region, or separation region in a single integrated device. Also provided is a device as described having one or more electrodes embedded in the body adjacent to one or more of the regions. The electrodes may be in dry or coated form. The body of the device may be surrounded by external, functional components such as electromotive sources, heaters, light sources, and optical detectors. The device may also be a component of a larger system, for example, a fluid flow cartridge that has other chemical processing functionalities. Such a cartridge is described in co-pending patent application PCT/US98/27632 filed Dec. 24, 1998 the disclosure of which is incorporated by reference herein.

The body may be a polymer, ceramic, or other material that permits the molding of chambers and channels directly into the material. The body may be of various shapes and sizes. The internal network of chambers and channels may be macro, meso or micro scale size, or a combination thereof. For example, the device may include a macro scale reaction chamber which leads to a microchannel transition region and separation region.

In general, the integrated device of the present invention includes one or more reaction chambers in fluidic communication with one or multiple separation regions through one or more transition regions. A variety of combinations of chambers, transition regions, and separation regions are intended to be within the scope of the invention. For example, a separation region may precede a reaction chamber and/or lead from the chamber. Also, multiple separation regions may be connected in series or in parallel. These separation regions may be of assorted types, each providing different separating functions. For example, a reaction chamber may lead through a transition region to a hybridization site which in turn leads to an electrophoresis channel.

Figure 1:
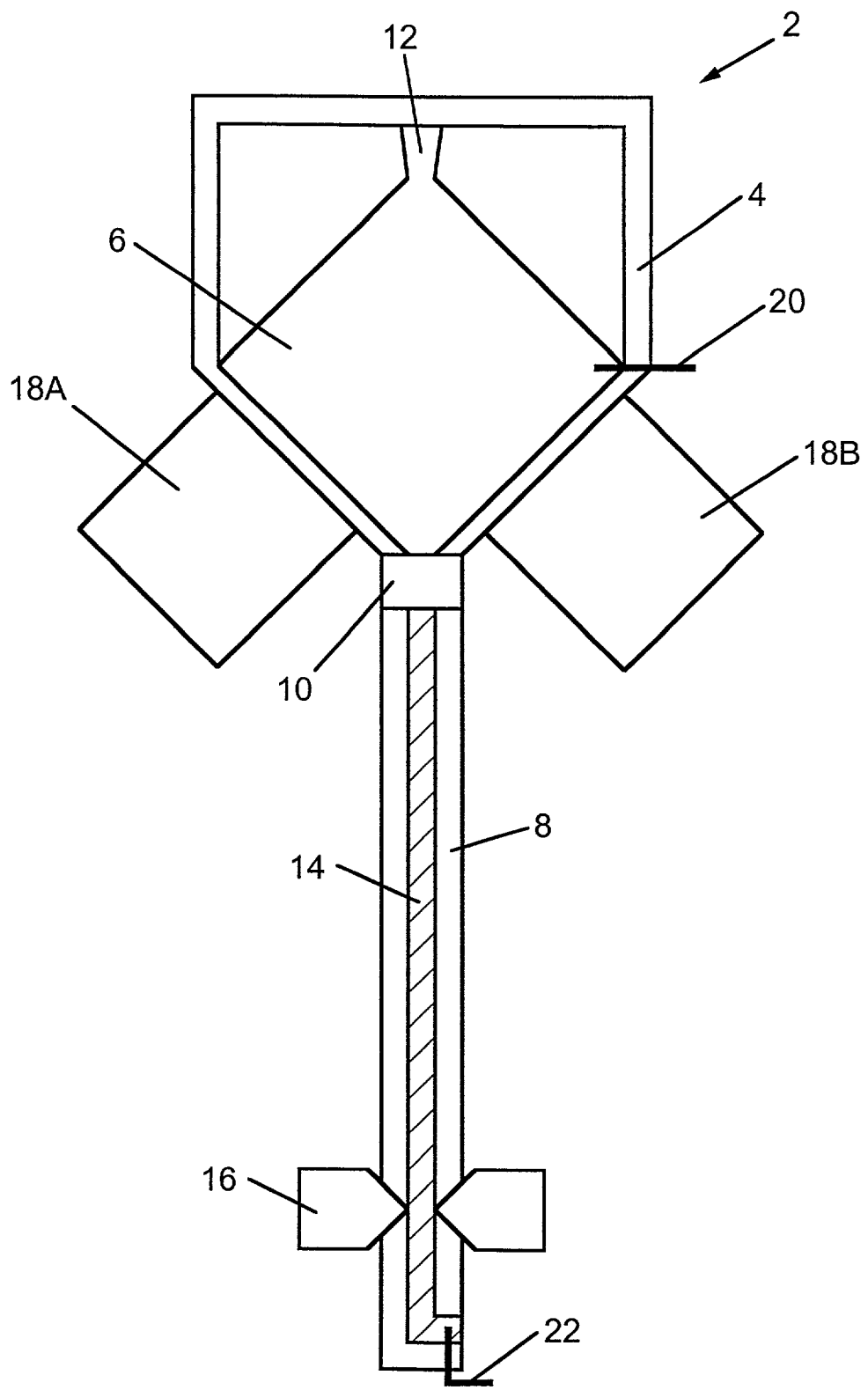
FIG. 1 is a schematic view of a processing device having an integrated reaction chamber, transition region, and capillary electrophoresis separation region according to one embodiment of the present invention.

FIG. 1 shows one embodiment of a processing device 2 formed by a body 4. The body 4 has formed therein a reaction chamber 6, a separation region 8, and a transition region 10 connecting the reaction chamber to the separation region. The reaction chamber 6 has an inlet port 12 for adding sample and reagents as required by the particular reaction performed in the chamber. The device 2 may include an outlet port as well as the inlet port 12. The ports may serve to connect the device to an external pump, vacuum source, or syringe. Alternatively, the ports may function as vents. In this embodiment, the separation region 8 is a capillary electrophoresis tube 14 containing appropriate separation material, e.g. electrophoresis gels or polymers, for separating components of the sample. Such separation materials are well known in the art.

The integrated device 2 also includes an injection electrode 20 and a separation electrode 22 embedded in the body 4. The electrodes 20 and 22 are located at opposite ends of the device to drive electrophoretic, electro-osmotic, or IEF ion flow through the separation region 8. Each electrode is preferably embedded in the body 4 such that one end of the electrode protrudes through an external surface of the body and such that the other end of the electrode protrudes into an internal region of the body.

In a preferred embodiment, the device 2 is used in combination with and designed to be inserted into an external instrument (not shown) having a heater for heating the reaction chamber 6 and having electrical connections for applying a voltage difference between the electrodes 20, 22. The instrument may optionally include an optical detector 16 for detecting separated components of the sample in separation region 8. Additionally, the instrument may include a pair of optics assemblies 18A, 18B for monitoring the reaction chamber 6. Suitable optics assemblies for use with the device of the present invention are disclosed in U.S. application Ser. No. 09/081,260 filed May 19, 1998 the disclosure of which is incorporated by reference herein.

The reaction chamber 6 is designed for the particular process being performed, such as PCR, LCR, isothermal nucleic acid amplification, self-sustained sequence replication, enzyme kinetic studies, homogenous ligand binding assays, affinity binding assays, chemical or temperature mediated lysis of target microorganisms, more complex biochemical mechanistic studies, the study of certain physiologic process and other synthetic and ligand binding processes. The volume capacity of the chamber depends on its application. In a preferred embodiment, for PCR applications, the chamber has a volume capacity between about 10 to 100 microliters. Thermal energy may be supplied to the reaction chamber 6 by coupling the portion of the body 4 forming the chamber to an external heater. Alternatively, a heating element may be permanently coupled to the body using screen-printing or thin-film depositing techniques.

In terms of the separation region 8, there may be electrophoretic, hybridization, or IEF functionalities, different filtrations, or other separation mechanisms, such as molecular sieving. Where the separation functionality is electrophoresis, the separation region 8 is preferably a capillary, as in FIG. 1. The separation region may contain an appropriate separation matrix such as a gel or other solution suitable for electrophoresis or IEF, as is known in the art. The solutions may include buffers, additives, polymeric agents, etc. In the preferred embodiment, the capillary tube 14 is between about 0.05 to 1.0 mm in diameter and 1–10 cm in length.

Figure 2:
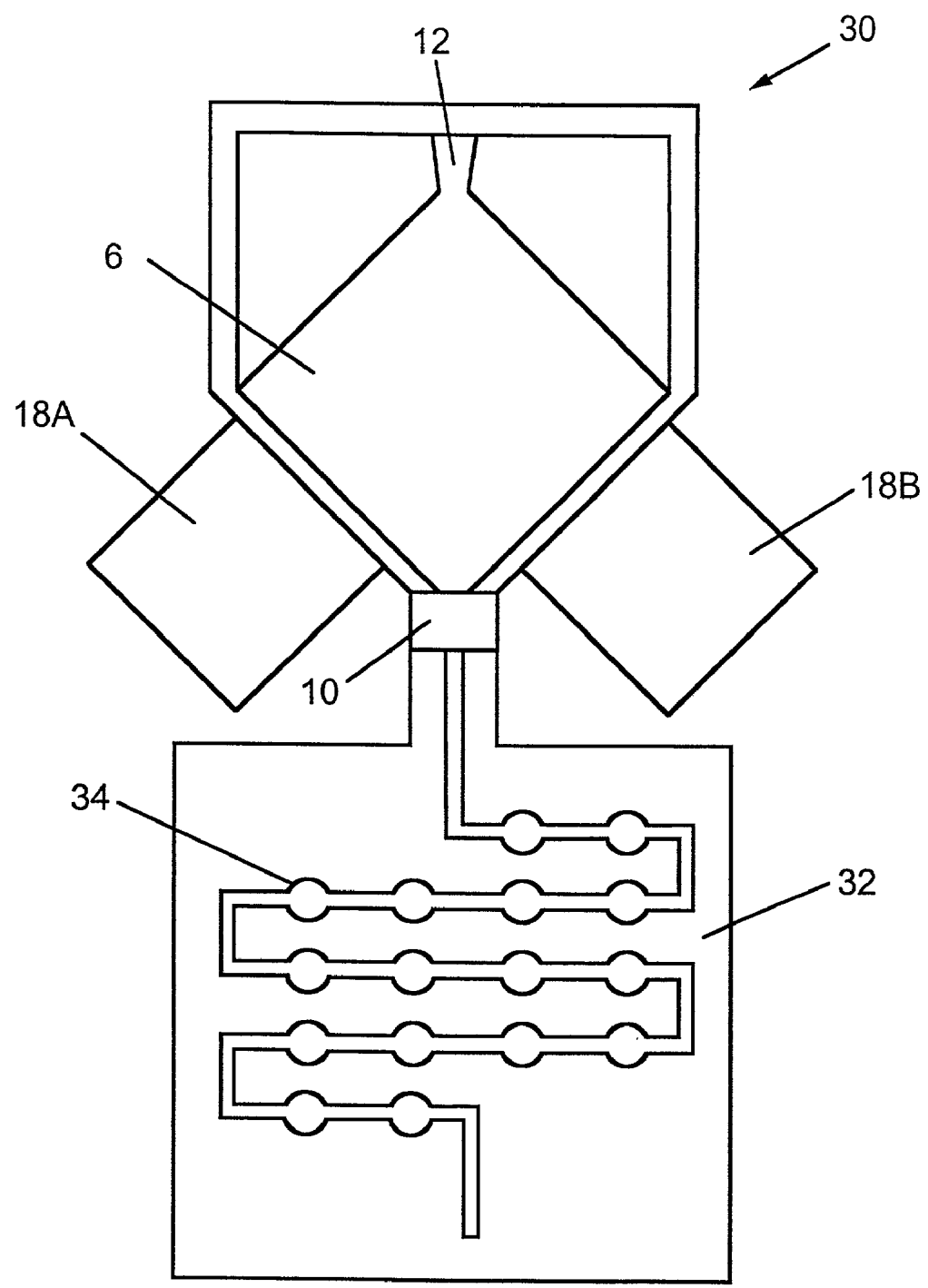
FIG. 2 is a schematic view of another processing device having an integrated reaction chamber, transition region, and hybridization separation region according to a second embodiment of the present invention.

FIG. 2 shows another embodiment of a processing device 30 in which the separation region 32 is a hybridization region incorporating an array of nucleic acid hybridization sites 34. Each hybridization site is preferably a channel or chamber coated with immobilized reagent such as polynucleotide probes. Immobilized reagent refers to reagent that is covalently or non-covalently attached to the surface of the structure. The immobilized reagent can be applied to the surface by a variety of methods well known in the art, e.g., dipping, inscribing with a pen, dispensing through a capillary tube or through the use of reagent jet-printing or any other suitable dispensing techniques.

Upon binding of the complementary analyte polynucleotide to the immobilized polynucleotide probe, a labeled probe, e.g., a fluorescent-labeled probe can be added to bind to the analyte polynucleotide. The amount of fluorescence is directly proportional to the amount of analyte in the test sample. Alternatively, the hybridization assay can be performed in a competitive format where a polynucleotide is conjugated to a detectable label. The polynucleotide labeled reagent competes with the analyte for binding to the immobilized polynucleotide. In another embodiment, the hybridization area comprises microstructure columns as described in co-pending application, U.S. Ser. No. 09/115,454 filed Jul. 14, 1998, the disclosure of which is incorporated by reference herein.

Other separation regions according to the present invention include ligand-binding sites in which members of a binding pair are located in the sites and couple to complementary binding pairs in the sample. In addition, the separation region may include selective filters such as molecular weight filters. Multiple functionalities may be located in one separation region. For example, electromotive separations such as electrophoresis may be combined with filters to pre-process certain samples where a mixture of protein background and nucleic acid is made to flow by electrical motive forces through a molecular weight cutoff filter, thereby filtering out the protein.

Figure 5:
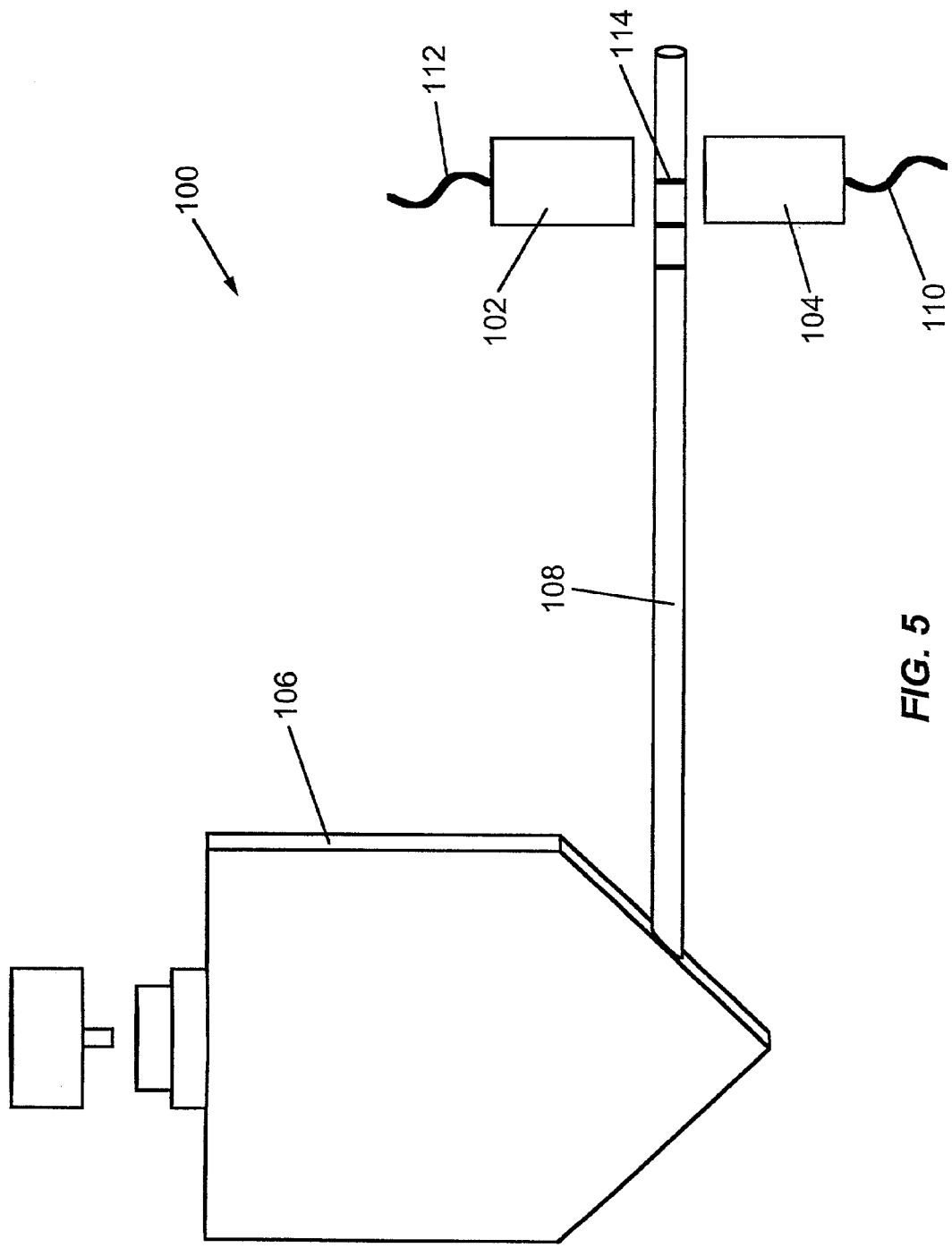
FIG. 5 is a perspective view of a chemical reaction and separation device according to a third embodiment of the invention.

Flow between the reaction chamber and the separation region may be by differential pressure, hydrodynamic forces, electrical motive forces, capillary action, pneumatic forces, hydraulic forces, mechanical forces, etc. The device may be coupled to instruments to actuate fluid flow such as pumps, vacuums, electrical connections, and the like. Electromotive mobility of molecules, and especially nucleic acids, as in isoelectric focus and electrophoretic mobility, is a convenient movement mechanism because of the predictability of movement. When conditions such as buffer ionic strength, channel dimensions, gel type and density, current density, voltage drop, time, etc. are constant, it is relatively easy to predict the location of molecules. Under controlled conditions, at time (T), the position of the analyte should be at position (X) consistently. This concept is illustrated in FIG. 5 in which site 114 denotes the location of the target.

For electrically motivated flow, a series of electrodes may be partially or fully embedded in the body of the device, or alternatively inserted prior to use. As shown in FIG. 1, electrodes 20, 22 may be actuated to induce fluid flow from the reaction chamber 6 to the separation region 8, or from the separation region 8 to the reaction chamber 6. Additionally, depending on the performance of the system and the requirements of the reaction chamber 6, a common electrode (not shown) located in or proximal to the transition region 10 may be included to drive the separation procedures. Both sample injection and electrophoresis can be achieved by applying a voltage between electrodes. The voltage may be applied by a power source external to the device. Alternatively, a suitable power source may be integrated into the device.

Prior to use, the device may have electrodes that are dry, coated, or pre-contacted with electrolytic fluids. In order to use the device, the electrodes should be exposed to electrolytes. Dry electrodes may be made to contact solutions by injecting fluids into the electrode regions or by releasing pre-disposed fluids from connecting reservoirs. Where the electrodes are coated, the coating may be dissolved by various means, to allow the electrodes to contact the electrolytic solution. Furthermore, the timing in which the coating of particular electrodes is dissolved may be controlled to control the activation of each electrode and thus dictate the resulting electrically driven movement of fluids or components.

There are numerous advantages to embedding electrodes in the body of the device. Embedded electrodes facilitate reproducibility of electrode position in each device, to allow one to achieve reproducible results among several devices. In addition, embedded electrodes permit mass production of such devices resulting in decreased cost of manufacture. Moreover, the disposable, single use device of the present invention avoids issues of electrode contamination which may occur where electrodes are permanently secured in multiple use devices and in contact with conducting fluids for a long period of time.

The electrodes may be embedded into the device with little additional cost by several techniques. First, metal electrodes can be situated inside a plastic injection molding production machine and "over-molded" during the injection molding process. Second, the metal electrodes may be selectively screen-printed, or otherwise deposited by plating, thin-film deposition, etc., and patterned on the body of the device. For example, one end of a screen-printed metal line may be used to contact fluid in the device while the other end forms a connector which is electrically engaged by an external instrument. Both of these techniques, and other similar techniques are cost-effective and very suitable for high-volume production lines. The electrodes are preferably located near vents which allow the venting of gases generated during the application of the high electric fields associated with electrophoresis. The vent ports could be simple openings in the tube itself or gas permeable hydrophobic membranes such as Gore-Tex®.

Another aspect of the processing device according to the present invention is the fluid transition region between the reaction chamber and separation region. In some embodiments, the transition region may be a simple fluidic connection, e.g. a tube, between the reaction chamber and the separation region. In other embodiments, the transition region includes valves, fluid inlet ports, mixing regions, and the like. In each embodiment, the transition region has a fluid flow restrictor, such as a viscous matrix, a constrictor, fluidic capacitor, ports, and/or at least one valve, which may be a mechanical two-way or three-way valve. The fluid flow restrictor is used to control the flow of fluid between the reaction chamber and separation region.

Figure 3A:
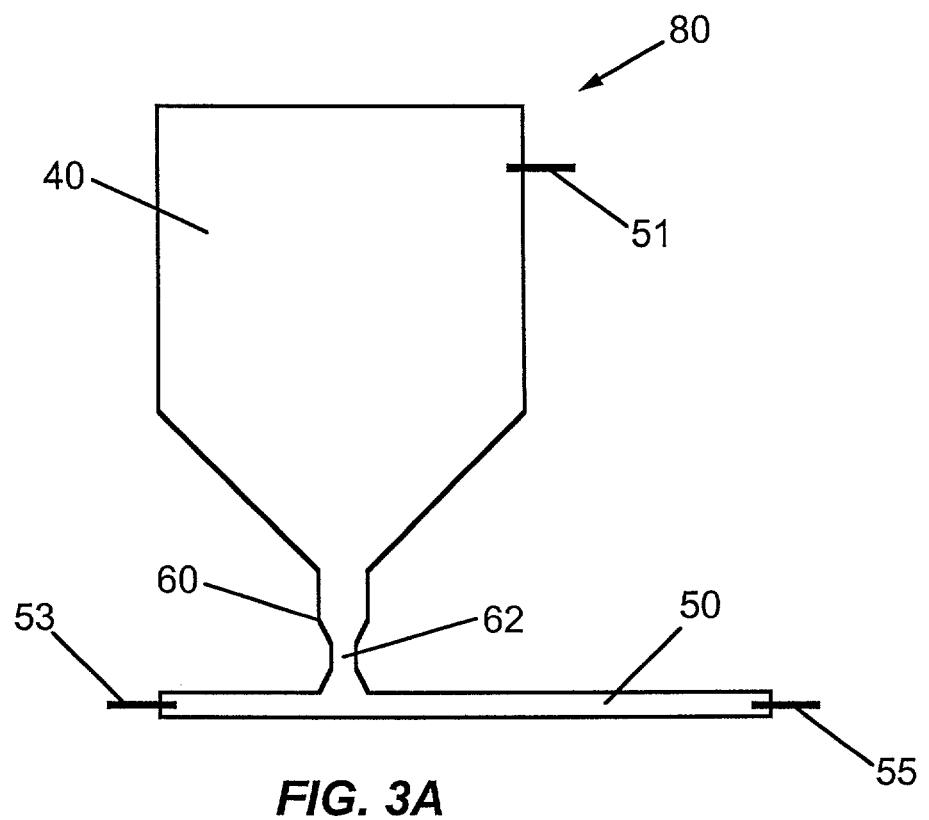
FIGS. 3A, B, C, D, E are schematic views of several variations of the transition regions connecting a reaction chamber and separation region according to the present invention.

FIGS. 3A–E show several embodiments of an integrated device from the perspective of the transition region 60 between the reaction chamber 40 and separation region 50. FIG. 3A shows a device 80 having a transition region 60 in which the flow restrictor is a constrictor 62. The inner diameter of the constrictor 62 is very narrow compared to the preceding area, e.g., the reaction chamber 40. The inner diameter of the constrictor 62 should be sufficiently small, preferably in the range of 0.01 to 1.0 mm, so that surface tension prevents the flow of fluid from the reaction chamber 40 to the separation region 50 until the electrodes 51, 53, 55 are activated.

Figure 3B:
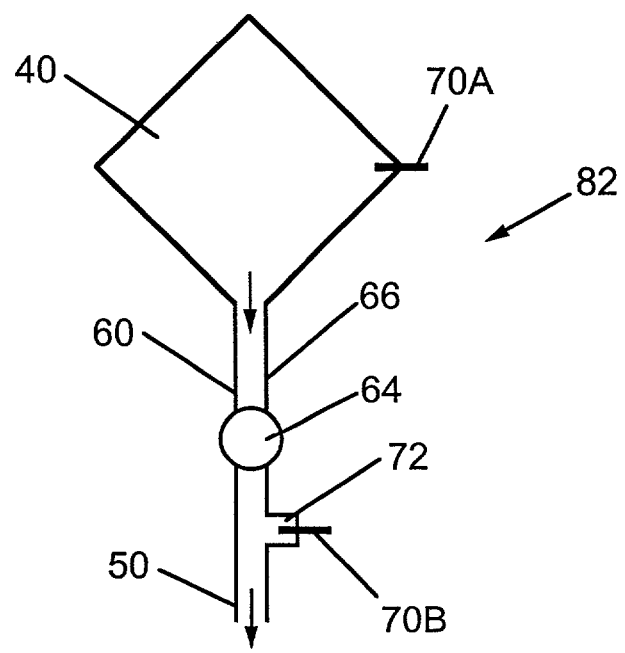
FIG. 3B shows a two-way valve.

FIG. 3B shows another exemplary device 82 having a two-way valve 64 located in transition region 60. This valve 64 may be an on-off valve, such as a pinch-off valve, a membrane valve, or the like, to prevent fluid from flowing through the valve when in a closed position and to permit fluid flow when in an open position. Fluids may be allowed to collect in a collection area 66 just upstream of the valve 64. In this manner, it may be possible to perform functions on the fluid sample prior to injection from the reaction chamber 40 into the separation region 50. For example, the valve 64 may be closed during nucleic acid amplification reactions in the reaction chamber 40, then opened just prior to sample injection into the separation region 50. Furthermore, it may be desirable to return the valve to a closed position to stop fluid flow and thus allow only a plug of fluid to pass into the separation region 50.

The valve 64 may also be used in the real-time monitoring of the processes occurring in the reaction chamber 40. As the reaction proceeds in the reaction chamber, a sample of fluid may be allowed to pass through the valve 64 by opening and closing the valve at selective intervals during the course of the reaction process. The fluid flows into the separation region 50 for separation of components and detection of chemicals, thus indicating the status of the reaction process at any given time. The detection of the sample may indicate that the reaction procedure should be adjusted to optimize results. For example, where nucleic acid amplification is occurring in the reaction chamber 40, if a low nucleic acid concentration is detected during the course of the amplification, the number of thermal cycles may be increased according to the desired outcome. Thus, a user of the device may avoid running too many or few cycles.

Electrodes positioned in the transition region and areas prior to the transition region, e.g., the reaction chamber 40, may facilitate movement of fluid into the transition region 60. Embedded electrodes 70A, 70B are shown by the form of the two-way valve configuration in FIG. 3C. The electrode 70A is embedded in the reaction region 40 and the second electrode 70B is embedded in a channel 72 immediately downstream from the valve 64. The electrodes 70A, 70B protrude through the body of the device to be partially exposed to the fluid inside of the chamber and channel.

Figure 3C:
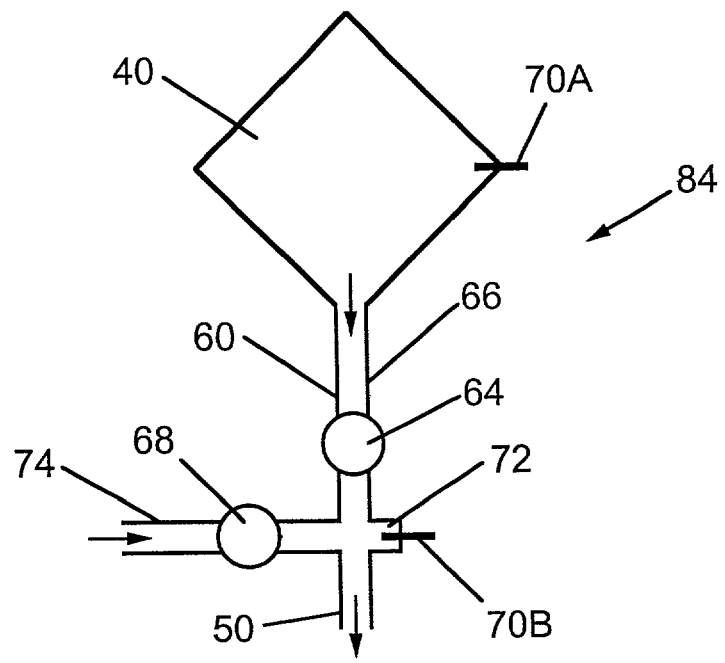
FIGS. 3C and 3D show multiple two-way valves with an inlet channel.
Figure 3D:
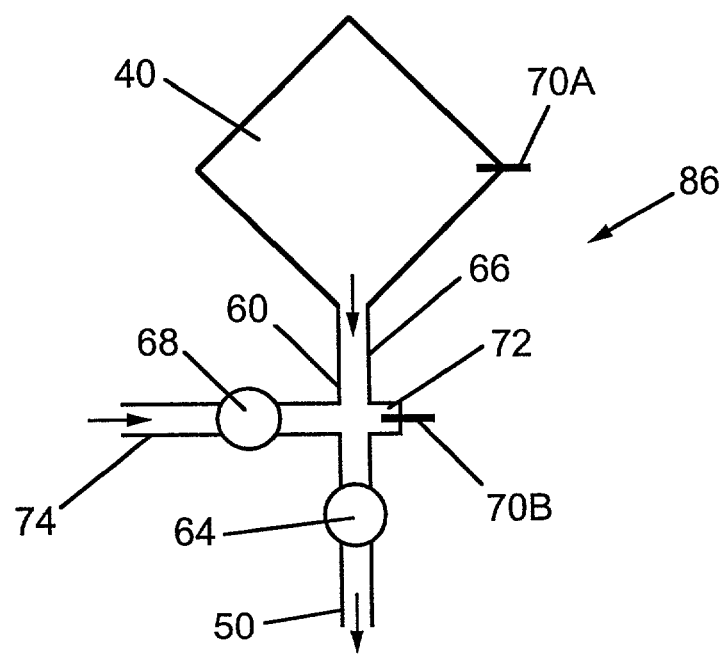

The embodiments of the transition region 60 shown in FIGS. 3C and 3D each include a combination of several two-way valves with a channel connected to the transition region. In these embodiments, a side valve 68 is located in a side channel 74 to control flow of fluids into the transition region 60. For example, reagents and fluids may be added to or channeled away from the separation region 60 through the side channel 74. These additional fluids may be injected prior to, during, or after the injection of the sample into the separation region 50. Functions such as washing, incorporation of ampholines for isoelectric focusing in the separation region 50, injection of markers, etc. may be utilized with such a channel and valve arrangement.

In the device 84 of FIG. 3C, the side channel 74 communicates with the transition region 60 downstream from the intermediary valve 64. In the device 86 of FIG. 3D, the side channel 74 communicates with the transition region 60 in the collection section 66 located upstream from the intermediary valve 64. In this embodiment, reagents may be allowed to interact with fluid in the collection section 66 prior to injecting the fluid into the separation region 50. Also in the embodiments of FIGS. 3C and 3D, the embedded common electrode 70B is positioned in the transition region 60 opposite the side channel 74. The common electrode 70B may have several functions. The common electrode may either work with a side electrode (not shown) in the side channel 74 to induce fluid flow from the side channel. In addition, the common electrode 70B may work with the injection electrode 70A to facilitate fluid flow from the reaction chamber 40.

Figure 3E:
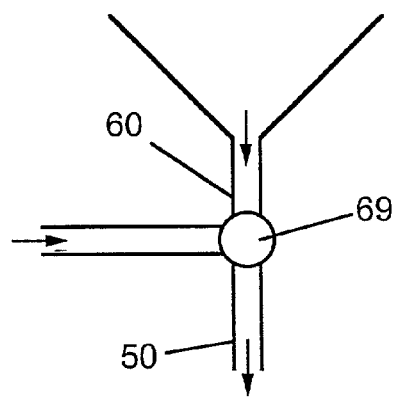
FIG. 3E shows a three-way valve.

Further to the types of valves in the transition region of the device, the function of multiple, two-way valves may be realized through a single three-way valve. FIG. 3E shows a device 88 having a three-way valve 69 that allows injection of additional fluids, e.g. reagents, into the transition region 60 through the side channel 74. A three-way valve or combination of two-way valves may also communicate with a concentration channel having a focusing gel and a common electrode. In this embodiment, a sample of chemicals flows into the channel to produce a fluid plug which may then be moved into the separation region.

Figure 4A:
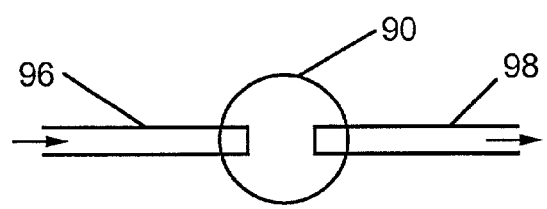
FIG. 4A is a plan view of an exemplary mechanical valve according to the present invention.
Figure 4B:
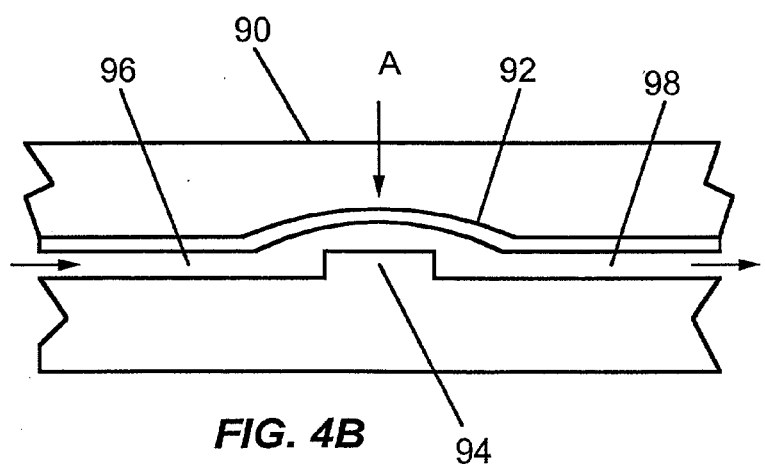
FIG. 4B is a cross-sectional view of the valve of FIG. 4A.

An exemplary membrane valve is shown in plan view in FIG. 4A and cross-sectional view in FIG. 4B. The membrane valve 90 comprises a thin flexible polymer layer 92 that can be exposed to a force A to bias the layer 92 against a surface 94 to seal the fluidic path between two channels 96 and 98. The valve 90 may then be released by removing the force A, causing the membrane to relax and permitting fluid to flow between the channels 96 and 98. The force A which deflects the flexible membrane may be pneumatically, hydraulically, or a mechanically induced, for example by a mechanical plunger.

Referring again to FIGS. 3A–3E, it is important that the transition region 60 thermally isolate the reaction chamber 40 from the separation region 50. This thermal isolation enables proper heating of a sample in the reaction chamber 40 and prevents the degradation of material in the separation region 50. The thermal isolation is achieved by making the transition region 60 thermally resistive, i.e., by ensuring that the transition region 60 has a lower thermal conduction than the reaction chamber 40. The thermal conduction of the transition region 60 relates to both the conductivity of the material forming the transition region and the size of the transition region relative to the reaction chamber 40. The present invention contemplates several methods for ensuring that the transition region 60 has a lower thermal conduction than the reaction chamber 40. First, the portion of the body defining the transition region 60 is made narrower than the portion of the body forming the reaction chamber 40 so that the transition region 60 substantially thermally isolates the reaction chamber 40 from the separation region 50. This is the presently preferred technique and is illustrated in the various embodiments of FIGS. 1–3E. Second, the transition region 60 may comprise a different material having a lower thermal conductivity than the material forming the reaction chamber 40. Third, thermal insulators, such as air pockets, may be formed in the body surrounding the transition region 60. Of course, suitable combinations of these techniques may also be employed.

One or more optical assemblies may communicate with the reaction chamber, separation region and/or other areas of the device. The optical assemblies may be externally coupled to the device and preferably include solid-state components, such as photodiodes and LEDs. As shown in FIG. 5, a device 100 includes a light source 102, such as an LED, and an optical detector 104, such as a lens, optical filter, and photodiode. Light source 102 and detector 104 are positioned to detect separated components, e.g. nucleic acid fragments, of the sample in the electrophoresis capillary 108. The nucleic acid fragments may be detected when stained with an intercalating dye such as ethidium bromide. An example of this format provides for ethidium bromide being added from a side channel (not shown) via electromotive forces of electrodes. The light source 102 is coupled to a controller by a connector 112 and data is received by the controller from detector 104 through a connector 110. The controller may comprise one or more microprocessors or microcontrollers for controlling operations such as fluid flow actuation, optics, detection, etc.

Alternatively, the optical detection system may comprise a laser and CCD. In this embodiment, the optical detection arrangement preferably includes an optical filter, such as an interference filter or band pass filter for passing the detection wavelength of interest, a CCD, focusing optics, a reflector/splitter, and an Argon ion laser. The operation is as follows: The laser excites the fluorescent indicator dye associated with product detection. The fluorescent signal is monitored by the CCD and passed to the controller. Alternatively, an LED may be used to excite the fluorescent indicator dye. Absorption spectroscopy could similarly be used.

Figure 6:
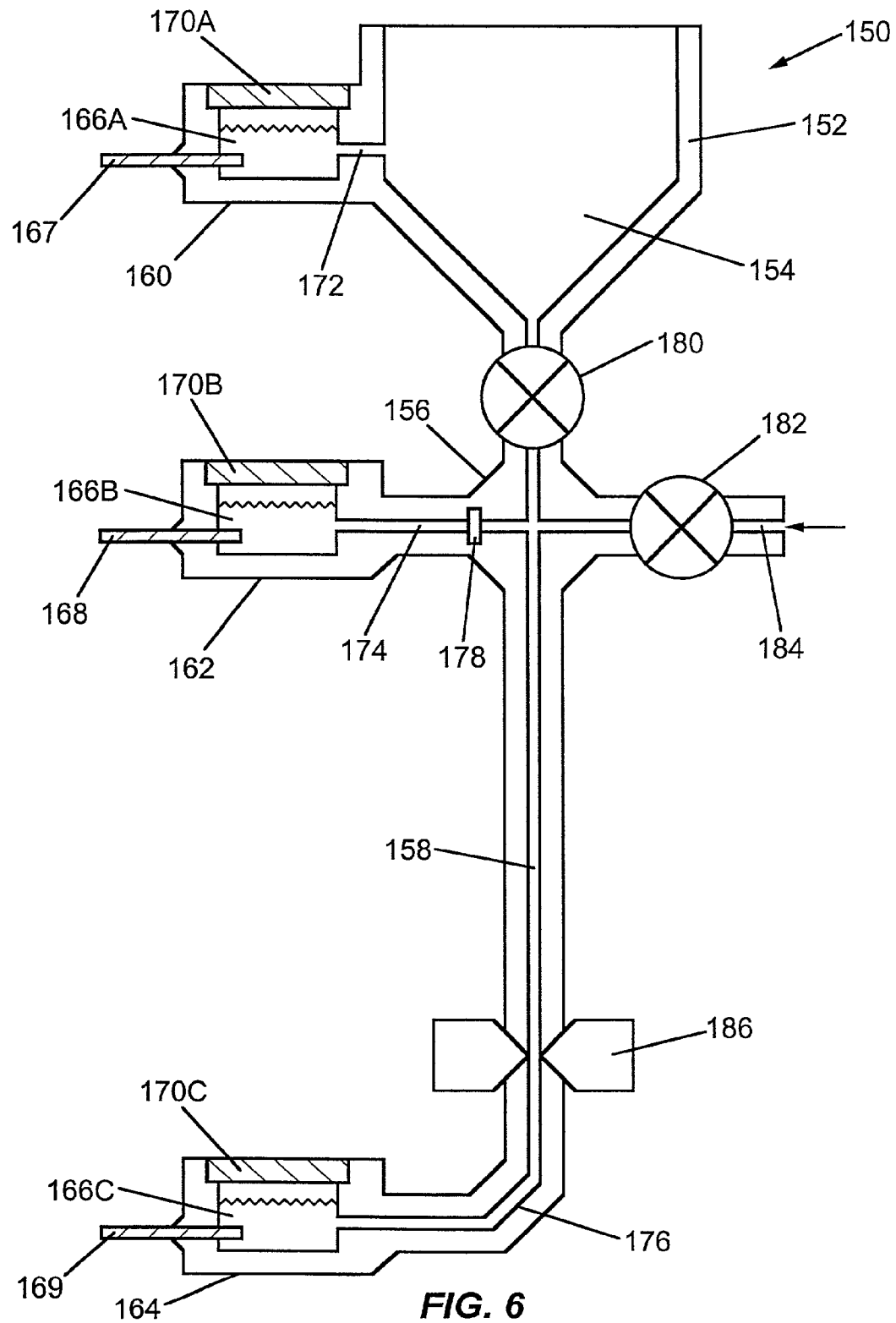
FIG. 6 is a schematic view of another chemical reaction and separation device according to a fourth embodiment of the present invention.

FIG. 6 illustrates another embodiment of the present invention in which a processing device 150 includes electrode regions 160, 162 and 164. Each electrode region includes a respective reservoir 166A, 166B, 166C for storing electrophoretically transported fluid. Each of the electrode regions also has a respective electrode 167, 168 and 169 embedded in the body 152 of the device. Each electrode protrudes through the body 152 to be partially immersed inside of a reservoir. Each reservoir further has a respective membrane 170A, 170B, and 170C to vent gases. The membranes may be made of Gore-Tex® or other convenient hydrophobic porous materials.

The first electrode region 160 is connected to a reaction chamber 154 by a channel 172. Similarly, the second electrode region 162 is connected to a transition region 156 by a channel 174. The channel 174 further includes a filter 178, preferably a high molecular weight filter, to allow only selected molecular components to pass. The third electrode region 164 is attached to the terminal end of a separation region 158 by a channel 176. A valve 180 in transition region 156 controls fluid flow from the reaction chamber 154 and a valve 182 controls cross-flow of fluid through a side channel 184. In a preferred embodiment, the device 150 is used for nucleic acid analysis and the reaction chamber 154 is a nucleic acid amplification chamber.

Examples of Operation

The present invention further contemplates particular methods for using various embodiments of the reaction and separation device described above.

1. Method for Using an Electrophoresis Device of the Present Invention:
   i) an unknown sample is mixed with the appropriate PCR, for example, mastermix solution and introduced into the reaction chamber portion of the analysis system;
   ii) a PCR reaction sequence (or other DNA amplification technique or chemical reaction) is performed on the solution inside the reaction chamber;
   iii) optical monitoring of the reaction products inside the chamber is performed to track the progress of the amplification reaction;
   iv) when it is determined that sufficient product, such as nucleic acid, has been generated inside the reaction chamber, the injection and common electrodes are activated, drawing a sample plug through the transition region into the top portion of the separation region, e.g., an electrophoresis tube containing a suitable gel. This electrophoretic injection step can be completed within a very short time, thereby minimizing the generation of bubbles within the reaction chamber;
   v) the common and electrophoresis electrodes are activated, causing the sample plug to drift through the gel and down the hollow separation tube;
   vi) as the separated bands of molecules traverse the length of the tube, they pass by the optical detection system and data representing the product is determined.

2. Method of Using the Electrophoresis Device Shown in FIG. 6:
   i) the sample and appropriate reagents are subjected to a nucleic acid amplification process in the reaction chamber 154, while valves 180 and 182 are closed;
   ii) optical monitoring of the reaction products inside the chamber 154 is performed to track the progress of the amplification reaction;
   iii) while valve 180 is closed, valve 182 is opened and an appropriate buffer solution is injected into the separation column or capillary 158 through the inlet port 184;
   iv) an appropriate electrophoresis voltage is applied between electrodes 167 and 168 while valve 180 is opened and valve 182 is closed. During this phase, high molecular weight species are collected on the high molecular weight filter 178;
   v) an appropriate electrophoresis voltage is then applied between electrodes 168 and 169, while valves 180 and 182 are closed. During this phase, the high molecular weight species collected on the filter 178 are electrophoretically transported down the separation capillary 158;
   vi) as the captured molecular species are electrophoretically transported down the capillary 158, they reach the optical detector 186 and are detected by optical fluorescence.

3. Method of Using a Device with a Hybridization Region and Three-way Valve:
   i) steps i) to iii) in Example 1 are performed on a sample;
   ii) a first three-way valve in the transition region is opened to allow the reaction mixture to flow under hydrodynamic force from the reaction chamber, through the valve, through a hybridization region (first separation region), through a second three-way valve, and into a connected waste area. As the fluid flows through the hybridization region, target molecules in the sample hybridize to capture ligands or probes covalently bound to the surface of the hybridization region;
   iii) the first three-way valve is switched to allow a reagent to flow hydrodynamically from a reagent access channel, through the first three-way valve, through the hybridization region, through the second three-way valve, and into the waste area. Reporter molecules or probes hybridize or bind to any target molecules captured in the prior step ii);

iv) a wash solution is introduced into the reagent access channel and flows through the hybridization region, through the second three-way valve and into the waste;

v) an elution solution is introduced into the reagent access channel and flows through the first three-way valve and into the hybridization region until the region is filled, at which time flow is stopped for a selected period of time;

vi) the second three-way valve switches to connect the hybridization area and a second access channel to a second separation region;

vii) the elution solution with the target molecules is eluted from the hybridization surface by chemical, thermal or electrical means;

viii) the elution solution with the target molecules resumes flow through the second three-way valve at the same time that a reagent is added through the second access channel where the elution and reagent meet and flow together into the second separation region;

ix) electrodes in communication with the second separation region are activated causing the target molecules to separate and migrate to their pI location;

x) a CCD camera optically images the entire length of the second separation channel to provide a barcode-like result.

4. Method of Using a Device with a Hybridization Region, Electrophoresis Region and Three-way Valve:

i) steps i) to vii) in Example 3 are performed on a sample;

ii) the elution solution with the target molecules resume flow through the second three-way valve;

iii) electrodes in communication with the second separation region are activated causing the elution solution with target molecules to flow into the separation region and the target molecules to separate in the matrix located in the second separation region;

iv) a CCD camera optically images the entire length of the second separation channel to provide a barcode-like result.

FABRICATION

The devices of the present invention may be produced by injection molding, casting, machining or other convenient means of making a one-piece body without bonding multiple pieces together. Molding allows for formation of a contiguous reaction chamber, transition region, and separation region. Valve structures may also be included in the mold, or in the alternative, added to device after the body is molded.

Although a one-piece body is presently preferred, a device of the present invention may also be produced by sealing or laminating one or more plastic films to a molded polymeric part. For example, the body of the device may comprise a molded polymeric part having the reaction chamber, transition region, and separation region formed therein and first and second plastic films sealed to opposite sides of the molded polymeric part to enclose the reaction chamber, transition region, and/or separation region. To aid in the transfer of energy to the sample components or to aid in optical detection of the components, it is preferred that the plastic films be relatively thin, e.g., that the films each have a thickness in the range of 0.01 to 0.5 mm, and more preferably have a thickness of about 0.05 mm.

The integrated devices of the present invention are preferably made of any number of polymeric materials. Included among these are, but not intended to be limited to, polyolefins such as polypropylene and polyethylene, polyesters such as polyethylene terephthalate, styrene containing polymers such as polystyrene, styreneacrylonitrile, and acrylonitrilebutadienestyrene, polycarbonate, acrylic polymers such as polymethylmethacrylate and poly acrylonitrile, chlorine containing polymers such as polyvinylchloride and polyvinylidenechloride, acetal homopolymers and copolymers, cellulosics and their esters, cellulose nitrate, fluorine containing polymers such as polyvinylidenefluoride, polytetrafluoroethylene, polyamides, polyimides, polyetheretherketone, sulfur containing polymers such as polyphenylenesulfide and polyethersulfone, polyurethanes, silicon containing polymers such as polydimethylsiloxane. In addition, the structures can be made from copolymers, blends and/or laminates of the above materials, as well as glass and ceramic materials.

Furthermore, electrodes may be "overmolded" by partially inserting electrodes at their selected locations into the mold such that the electrodes become embedded in the body after the material is added to the mold and allowed to solidify. The electrodes may be made of platinum, silver, carbon, gold or any other suitable electrically conductive material. Other components may be optionally overmolded to the device in a similar fashion.

In the alternative, after the body is formed, electrodes, filters, resistive heating elements, etc. may be embedded into the body using screen-printing or thin-film depositing techniques. Reagents, matrices or fluids maybe injected into various reservoirs and channels of the formed body. Furthermore, the device may include components external to the body, such as optics, electrical connections to the electrodes, heater(s) embedded in the body, pneumatic interfaces to pumps or vacuums, etc. Alternatively, such components may be located in an external instrument into which the device is placed for sample processing, as described above.

To summarize, the entire assembly of the reaction chamber, transition region, and separation region are preferably formed in a single, disposable body. There are a number of reasons why the device of the present invention is much improved over prior implementations.

1) the entire device is disposable, so that sample carryover and contamination from sample to sample is not a problem;
2) all major elements of the device are integrated into one analytical component; it is not necessary to transfer the sample or the reaction products from one device having a reaction chamber to a separate device having a separation tube;
3) provision is made for thermally isolating the reaction chamber from the separation region, thereby ensuring proper heating of a sample and operability of the separation region;
4) provision is made for optical detection both in the reaction chamber as well as the separation tube;
5) provision is made for venting and otherwise dealing with the gases generated during electrophoresis or during isoelectric focusing;
6) the inconvenience of bonding techniques to connect substrates and modules is avoided; and
7) embedded electrodes provide for reproducibility and low cost mass production.

The present invention has been described above in varied detail by reference to the particular embodiments and figures. It is to be understood that modifications or substitutions may be made to the devices and methods described based upon this disclosure without departing from the broad scope of the invention. Therefore, the scope of the invention should be determined by the following claims and their legal equivalents.

What is claimed is:

1. A device for analyzing a sample, the device comprising:
 a) a body having:
  i) a reaction chamber for chemically reacting the sample;
  ii) a separation region for separating components of the sample;
  iii) a transition region connecting the reaction chamber to the separation region; and
  iv) at least one mechanical valve in the transition region for controlling fluid flow between the reaction chamber and the separation region;
 b) a first electrode coupled to the body adjacent the reaction chamber;
 c) a second electrode coupled to the body adjacent the transition region; and
 d) a third electrode coupled to the body adjacent the separation region, the electrodes being positioned such that when a first voltage is applied between the first and second electrodes, the components in the sample are transported from the reaction chamber to the transition region, and such that when a second voltage is applied between the second and third electrodes, the sample components are transported into the separation region.

2. The device of claim 1, further comprising a molecular weight filter for filtering species in the sample having a sufficiently high molecular weight, the filter being positioned in a channel between the second electrode and the transition region such that when the first voltage is applied between the first and second electrodes, the species are transported from the reaction chamber and collected on the filter, and such that when the second voltage is applied between the second and third electrodes, the species collected on the filter are transported into the separation region.

3. The device of claim 1, wherein the body further includes:
 a) a side channel connected to the transition region for adding or removing fluid from the transition region; and
 b) at least a second mechanical valve for controlling fluid flow through the side channel.

4. The device of claim 3, wherein the valves comprise membrane valves.

5. The device of claim 1, wherein the body comprises a polymeric material, and wherein the electrodes are overmolded in the body.

6. The device of claim 1, wherein the electrodes are screen-printed on the body.

* * * * *